United States Patent [19]

Spears

[11] Patent Number: 4,512,762
[45] Date of Patent: Apr. 23, 1985

[54] METHOD OF TREATMENT OF ATHEROSCLEROSIS AND A BALLOON CATHETER FOR SAME

[75] Inventor: James R. Spears, Boston, Mass.
[73] Assignee: The Beth Israel Hospital Association, Boston, Mass.
[21] Appl. No.: 443,958
[22] Filed: Nov. 23, 1982
[51] Int. Cl.³ .................................................. A61B 6/08
[52] U.S. Cl. .................................... 604/21; 604/53; 128/666; 128/303.1; 128/398
[58] Field of Search ................... 604/20, 21, 49–53, 604/96–100; 128/303.1, 303.11, 325, 344, 630, 653, 654, 656, 658, 665, 666, 398

[56] References Cited

U.S. PATENT DOCUMENTS

| | | | |
|---|---|---|---|
| 3,494,354 | 2/1970 | Yokota et al. | 128/398 |
| 3,557,783 | 1/1971 | Castner | 604/20 |
| 3,661,148 | 5/1972 | Kolin | |
| 4,266,549 | 5/1981 | Kimura | 128/303.1 |
| 4,315,512 | 2/1982 | Fogarty | 604/97 |
| 4,323,071 | 4/1982 | Simpson et al. | 604/53 |
| 4,336,809 | 6/1982 | Clark | 128/303.1 |
| 4,384,584 | 5/1983 | Chen | 604/98 |

OTHER PUBLICATIONS

*Aqueous Peroxyoxalate Chemiluminescence*, Final Report to the Office of Naval Research, Contract N00014-77-C-0634, A. Mohan et al., Discovery Research Department, Chemical Research Div., American Cyanamid Company, Bound Brook, NJ, pp. 1–156 (Jan. 1982).
"Atherosclerosis", H. Wolinsky, *Cardiovascular Diseases* (U.S.A.), vol. XIV, pp. 1218–1222.
"The Photodynamic Properties of a Particular Hematoporphyrin Derivative", R. Lipson et al., *Archives of Dermatology* (U.S.A.), vol. 82, No. 4, pp. 76/508–84/516 (1960).
R. Lipson et al., "Hematoporphyrin Derivative for Detection and Management of Cancer", *Cancer* (U.S.A.), vol. 20, No. 12, pp. 2255–2257 (Dec. 1967).
R. Lipson et al., "The Use of a Derivative of Hematoporphyrin in Tumor Detection", Journal of the National Cancer Institute (U.S.A.) vol. 26, No. 1, pp. 1–8 (Jan. 1961).
D. Sanderson et al., "Hematoporphyrin as a Diagnostic Tool", (U.S.A.), vol. 30, No. 5, pp. 1368–1372 (Nov. 1972).
*Cancer Therapy Abstracts* (U.S.A.), 79–0299, T. Dougherty, "Photoradiation in the Treatment of Recurrent Breast Carcinoma", p. 69 (1979).
*Cancer Therapy Abstracts* (U.S.A.), 79–0463, T. Sery, "Photodynamic Killing of Retinoblastoma Cells with Hematoporphyrin and Light", pp. 160–161 (1979).
*Cancer Therapy Abstracts* (U.S.A.), 79–2363, J. Moan, "The Mechanism of Photodynamic Inactivation of Human Cells in Vitro in the Presence of Haematoporphyrin", pp. 735–736 (1979).
F. Gollan et al., "Oxygen Transport of Colloidal Fluorocarbon Suspensions in Asanguineous Rabbits," *American Journal of Physiology* (U.S.A.), vol. 229, No. 4, pp. 1045–1049 (Oct. 1975).

(Continued on next page.)

*Primary Examiner*—C. Fred Rosenbaum
*Assistant Examiner*—Michelle N. Lester
*Attorney, Agent, or Firm*—Anthony M. Lorusso

[57] ABSTRACT

A method for the treatment of atherosclerosis in a mammal by destruction of atheromatous plaque is disclosed. The disclosed method includes injecting a hematoporphyrin into the mammal for selective uptake into the atheromatous plaque, and delivering light to the diseased vessel so that the light activates the hematoporphyrin for lysis of the plaque. The preferred method utilizes a balloon catheter equipped with flexible optical fibers for transmission of light from an external source for illumination of the interior of the inflated balloon. By inflation of the balloon, the opaque blood between the balloon and the atheromatous plaque is displaced to facilitate activation of the hematoporphyrin. The balloon may be illuminated and inflated and deflated in a cycle responsive to the patient's pulse so as to minimize interference with blood flow.

8 Claims, 2 Drawing Figures

OTHER PUBLICATIONS

K. Kanter et al., "Superiority of Perfluorocarbon Cardioplegia Over Blood or Crystalloid Cardioplegia," *Circulation* (U.S.A.), vol. 64, Supplement II, pp. II-75-II-80 (Aug. 1981).

"Fluorescence of Experimental Atheromatous Plaques with Hematoporphyrin Derivative", J. Richard Spears, Juan Serur, Deborah Shropshire and Sven Paulin *J. Clin. Invest., 71:395–399 (1983)*.

"In Vivo Coronary Angioscopy", J. Richard Spears, H. John Marais, Juan Serur, Oleg Pomerantzeff, Robert Geyer, Robert S. Sipzener, Ronald Weintraub, Robert Thûrer, Sven Paulin, Richard Gerstin, William Grossman, *J. Am. Coll. Cardiol.*, 1:1311–1:1314 (1983).

METHOD OF TREATMENT OF ATHEROSCLEROSIS AND A BALLOON CATHETER FOR SAME

BACKGROUND OF THE INVENTION

Atherosclerosis is a coronary disease wherein fatty substances (lipids), hereinafter referred to as atheromatous plaques, form deposits in and beneath the intima which is the innermost membrane lining arteries and veins. Atherosclerosis tends to involve large and medium-sized arteries. Most commonly affected are the aorta and the iliac, femoral, coronary, and cerebral arteries. Clinical symptoms occur because the mass of the atherosclerotic plaque reduces blood flow through the involved artery and thereby compromises tissue or organ function distal to it.

Modern treatment of atherosclerosis revolves around highly sophisticated coronary care units. In general, modern medicine follows one of two approaches to the care of patients suffering from atherosclerotic complications: either (1) the diseased vascular segments are replaced with prosthetic or natural grafts, even going as far as heart transplantation or (2) drugs such as antiarrhythmic agents, anticoagulants and plasma lipid lowering agents are administered to enable the patient to live with the condition. Neither approach contemplates a cure of the diseased members.

SUMMARY OF THE INVENTION

The present invention provides for treatment of a main artery or other blood vessel afflicted with atherosclerosis. The method involves administration of a hematoporphyrin, preferably by intravenous injection, to the mammal to be treated. The invention resides, in part, in the discovery that the hematoporphyrin so administered is selectively absorbed into the atheromatous plaque, with little or no absorption into healthy areas of the arterial wall. Upon illumination of the atheromatous plaque, containing absorbed hematoporphyrin, the hematoporphyrin is activated and destroys the host atheromatous plaque tissue. Illumination of the plaque may be achieved with either one of two different techniques. With one technique, the patient is catheterized with a light-emitting catheter inserted into the diseased artery or other vessel so that the light-emitting portion of the catheter is adjacent the atheromatous plaque. Alternatively, a form of liquid light is injected into the vascular tree such that the liquid light, which mixes freely with blood or a blood replacement, perfuses the diseased artery.

In the preferred embodiment a special light-emitting balloon catheter is employed. The balloon catheter includes an inflatable balloon secured to one end of the catheter tube, for inflation of a gas from a remote source, and optical fibers which extend through the tube lumen for transmission of light from an external light source to the interior of the balloon. Preferably, the light-transmitting optical fibers are optically joined to a light scattering device within the balloon in the form of a hollow, liquid-filled fiber or tube. The liquid filling is selected for optimum transmission of light and maximum light scattering.

Use of the preferred balloon catheter provides for displacement of the light-opaque blood between the external balloon surface and the atherosclerosis plaque by inflation of the balloon. Use of the preferred catheter also allows for intermittent and cyclical illumination and inflation/deflation of the balloon so as to minimize interruption of blood flow to the vital organs and to avoid potential problems attendent to heating of the balloon material and the blood of the mammal undergoing treatment.

Activation of hematoporphyrin within atheromatous plaques may also be achieved by injecting a form of liquid light into the vascular tree. Examples of light-emitting liquids are the bioluminescent system of firefly lucerin/lucerase and the chemiluminescent system of the Cyalume Lightstick manufactured by the American Cyanamid Company. Although the organic liquid-based Cyalume Lightstick is incompatible with blood, an aqueous liquid-based chemiluminescent system has recently been developed. See "Aqueous Peroxyoxalate Chemiluminescence, Final Report to the Office of Naval Research, Contact N00014-77-C-0634" by A. G. Mohan et al. at the American Cyanamid Company, Bound Brook, N.J., January, 1982. Although the light intensity of any liquid light is less than that which is achievable with the fiberoptic delivery of a laser, activation of hematoporphyrin is a function of the product of light intensity times the duration of illumination, so that a relatively low level of light intensity for a long duration is sufficient to activate hematoporphyrin. A potential advantage of the use of liquid light is that all diseased vessels can be perfused with the liquid light, once intravascular injection of the liquid light and mixing with blood have been completed. Knowledge of the exact location of atheromatous plaques would be unnecessary, since all plaques would be exposed to the light. Should blood prove to be too light-opaque to allow a sufficient quantity of light to reach a plaque, blood replacement with more translucent liquids, such as perfluorocarbon emulsion-containing blood substitutes, may be performed prior to injecting the liquid light. For an example, in animals, of total blood exchange with perfluorocarbon chemicals, see Gollan et al, *Am J. Physiol* 229:1045 (1975). Fluosol-DA, a commercially available perfluorocarbon-containing blood substitute from Alpha Therapeutics, a subsidiary of the Green Cross Corporation, is currently undergoing clinical trials and has been used for massive transfusions in patients with a remarkable lack of side effects.

Since both the firefly luciferin/lucerifase system and the aqueous peroxyoxylate system can be too toxic in the doses that are required to activate hematoporphyrin within atheromatous plaques, the toxicity of these systems can be reduced markedly by modifications such as microencapsulation of some or all of the reactants in these liquids.

Accordingly, it is an object of the present invention to provide a method for treatment of atherosclerosis by destruction of the atheromatous plaque.

It is a further object of the present invention to provide a catheter for transmission of activating light directly into atheromatous plaque by displacement of light-opaque blood between the light-emitting portion of the catheter and the atheromatous plaque.

It is yet a further object of the present invention to illuminate atheromatous plaques, containing absorbed hematoporphyrin, with minimal interruption of the flow of blood to the vital organs.

Yet another objective is to illuminate atheromatous plaques with minimal elevation of the temperature of the mammal's blood.

Yet another objective is to illuminate atheromatous plaque by perfusing the diseased vessel with liquid light.

Other objects and further scope of applicability of the present invention will become apparent from the detailed description to follow, taken in conjunction with the accompanying drawings.

DESCRIPTION OF THE PREFERRED EMBODIMENTS

Figure 1:
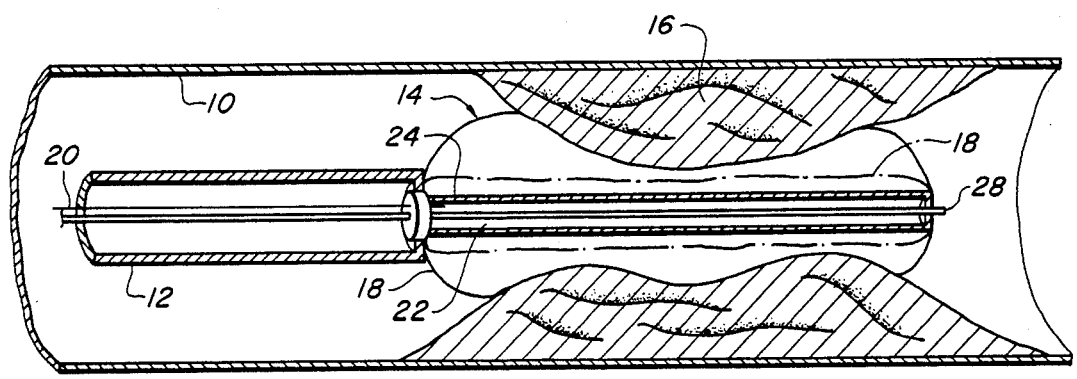
FIG. 1 is a schematic representation of use of the preferred catheter, inserted into a main artery of a patient, for treatment of atherosclerosis in accordance with the present invention.

The term "hematoporphyrin", as used herein, is intended to encompass hematoporphyrin and its derivatives which are preferentially taken up into atheromatous plaque and which respond to a source of light to destroy the host cell tissue.

The preferred hematoporphyrin is the acetic acid-sulfuric acid derivative of hematoporphyrin prepared, for example, as described by Richard L. Lipson and Edward J. Baldes in "The Photodynamic Properties of a Particular Hematoporphyrin Derivative", *Arch. Derm.* 82(4) 508-516, 1960 and by Richard L. Lipson et al in "The Use of a Derivative of Hematoporphyrin in Tumor Detection", *J. Natl. Cancer Inst.* 26(1):1-8, 1961. In general the method of Lipson et al involves admixing a "crude" recrystallized hematoporphyrin with a mixture of 19 parts glacial acetic acid and one part concentrated sulfuric acid, followed by filtration to separate and remove the undissolved residue. The solution is then neutralized, e.g. with a 3% sodium acetate solution, to precipitate out the hematoporphyrin derivative (HPD). This hematoporphyrin derivative is recognized by the trade designation HPD and is commercially available from Oncology Research and Development, Inc. In practicing the present invention, the HPD is used in the commercial form and is not diluted in any way.

Sanderson et al, in "Hematoporphyrin as a Diagnostic Tool" *Cancer* 30(5) 1368-72 (1972) report that this hematoporphyrin derivative (HPD) shows maximum fluorescence upon illumination with violet light within a wave length range of about 400 to 410 nm. HPD exhibits wide band absorbtion at about 500 nm with small peaks at about 635 nm. For the purposes of the present invention, the preferred activating illumination for the hematoporphyrin derivative (HPD) is a monochromic red light at about 635 nanometers because light at this wavelength penetrates tissue; and, the preferred source for such illumination is a dye laser.

It has been well known for many years that HPD accumulates in malignant tumors after intravenous injection and that HPD fluorescence, upon exposure to ultraviolet light, facilitating tumor localization. The aforementioned articles by Lipson et al report on such findings. More recently, the cytotoxic effect of HPD activated by light has been used to destroy malignant tumors in man as well as in animals. Since normal tissues surrounding malignant tumors absorb relatively small amounts of HPD, little or no damage to these tissues occurs upon exposure to light. See, e.g. "Photoradiation in the Treatment of Recurrent Breast Carcinoma", T. J. Dougherty et al, *J. Natl, Cancer Inst.* 62(2):231-237 (1979).

In accordance with the present invention, it recently has been discovered that HPD is selectively concentrated in atheromatous plaques in the aorta of rabbits following intravenous injection. Atheromatous plaques were found to fluoresce strongly when exposed to ultraviolet light, while the normal plaque-free aortic wall demonstrated no fluorescence. Since atheromatous plaques consist primarily of cells which are engorged with lipids and other materials, destruction of these cells by photoactivation of HPD results in lysis of such plaques. It is believed that, upon exposure to activating illumination, the hematoporphyrin produces singlet oxygen which causes cell destruction. Thus, the present invention involves photodynamic destruction of the atheromatous plaques by activation of plaque-absorbed hematoporphyrin by a process which may be characterized as photoatherolysis.

The preferred catheter of the invention is illustrated in FIG. 1. In the representation of FIG. 1 the wall of the main artery undergoing treatment is represented by the numeral 10. For treatment, the mammal is catheterized with insertion of the light-emitting portion of the catheter into the diseased blood vessel to a position adjacent the deposit of atheromatous plaque to be lysed. FIG. 1 depicts the preferred catheter positioned in this manner. The preferred catheter includes a lumen tube 12 and a balloon member 14 affixed to its distal end with the interior of the balloon opening into the lumen of the catheter tube. FIG. 1 depicts the balloon 14 in its inflated state with its exterior surface in direct contact with the atheromatous plaque 16 to be lysed. The deflated state of the balloon is indicated by the dotted line 18. Inflation of the balloon is provided for by the lumen of the catheter which is in fluid communication with the interior of the balloon and which may be connected, at its opposite end, to a source of pressurized gas. At least one optical fiber 20 is provided for transmitting light from an external source to liquid 22 contained in a hollow glass fiber 24. The liquid 22, for example one of many refractive index liquids commercially available from Cargille Laboratories, functions to transmit and scatter light throughout the interior of balloon 14. A movable guidewire 28 extends through the center of the lumen of the catheter tube and through the center of the hollow glass fiber. The distal end of the guidewire 28 extends a variable distance beyond the distal end of the balloon 14.

Figure 2:
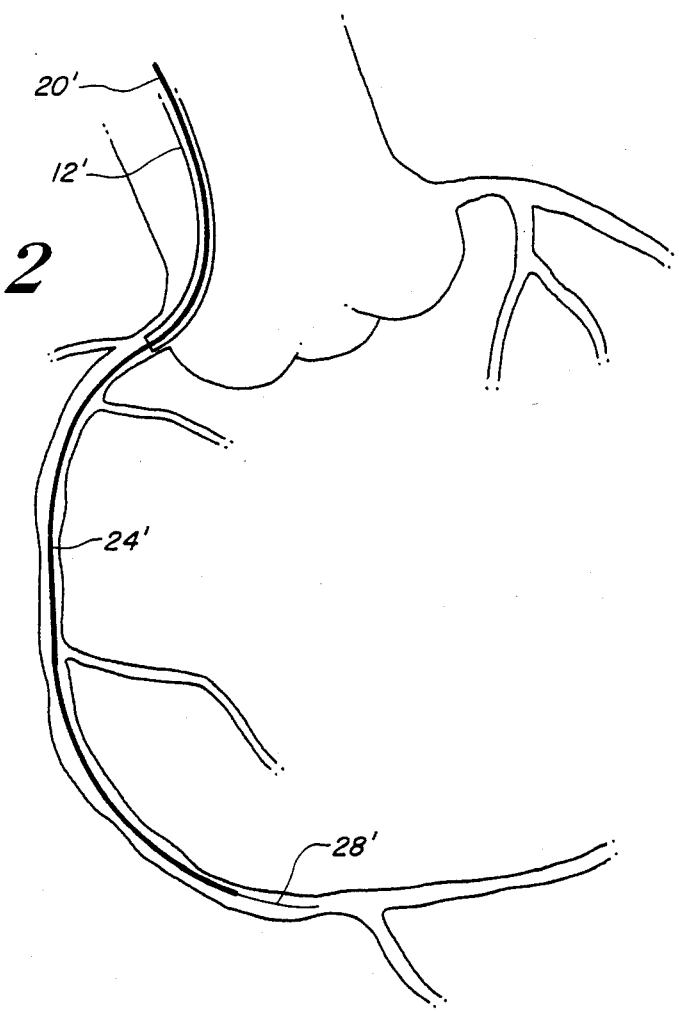
FIG. 2 is a schematic representation of the use of a second type of illuminating catheter in the treatment of atherosclerosis in accordance with the present invention.

FIG. 2 depicts the use of a catheter which is not provided with a balloon but which is otherwise similar. In FIG. 2, corresponding components of the catheter are represented by like numerals. A catheter of this design may be particularly advantageous for use in small vessels, such as coronary arteries, wherein displacement of the relatively small volume of blood with a balloon may be unnecessary for light to be transmitted to a plaque.

A particularly advantageous feature of the preferred catheter illustrated in FIG. 1 is the capability for delivering light to the plaque in an intermittent fashion. Intermittent light transmission, synchronized with intermittent balloon inflation, is advantageous when a prolonged exposure of a plaque to light within and to a vital organ is required. For example, inflation of the balloon with a low viscosity gas during only one part of each cardiac cycle, may be performed utilizing counterpulsation circulatory assist devices, and can be synchronized with light transmission, so that a long total, additive exposure of a plaque to light may be achieved without significant compromise of blood flow. Although light may be transmitted continuously along the optical fiber and exposure of the plaque to light would then occur only when inflation of the balloon is sufficiently great to displace intervening blood, intermittent transmission of the light along the fiber would be advantageous when the light intensity required would result in heating the balloon material and/or blood. For example, a thick plaque may require an intense light in order to activate HPD deep within the plaque. The heat produced by the light could adversely affect the balloon material and/or blood within the artery. Intermittent transmission of light would allow both the balloon material and the gas within the balloon to be cooled intermittently by the flow of blood past the balloon during balloon deflation. A period of 30 minutes or more may be required to photoactivate HPD deep within a plaque. However, obstruction of blood flow with the balloon inflated continuously for such a length of time cannot be performed within arteries to vital organs without deleterious effects. In such a case ECG-gated, intermittent balloon inflation, as is commonly performed with an intra-aortic balloon used in a counterpulsation circulatory assist device, may be employed so as not to interfere with blood flow to vital organs, while at the same time permitting a prolonged exposure of a plaque to light.

Others skilled in the art of fabrication of optical fibers and catheters may proffer many modifications of the basic design of the preferred catheter. For example, the optical fiber 20 may terminate without coupling to any other fiber; a properly designed lens at the terminal end of the optical fiber 20 might be used to disperse light over the internal surface of the artery. Alternatively, the optical fiber 20 may be coupled, at its distal end, to a specially designed solid fiber which would be used to disperse light along all or a portion of its length.

In accordance with the present invention, it has been discovered that aqueous peroxyoxylate chemiluminescent liquids manufactured by the American Cyanamid Company may be injected into the bloodstream of rats and rabbits without producing any side effects. The liquid reactants typically include a triflyl oxamide and hydrogen peroxide along with sulfonated rubrene as a fluorescer and Deceresol NI as a surfactant. A quantum yield of the reaction of 7% with a light capacity of 62 lumen hours per liter of solution was reported recently by A. G. Mohan et al in "Aqueous Peroxyoxalate Chemiluminescence: Final Report to the Office of Naval Research, Contract N0014-77-C-0634." This quantity of light is considerably more than that needed to activate hematoporphyrin. Thus, the injection of the chemiluminescent liquid light into the vascular tree of mammals can be performed for activation of hematoporphyrin within atheromatous plaques for lysis all of plaques throughout the vascular tree.

Another form of liquid light which can be injected into the bloodstream of mammals is the well-known firefly luciferin/lucerifase bioluminescent system. Luciferin and luciferase are water soluble, and light is emitted when adenosine triphosphate, which is also water soluble, is added to these substances. A buffer such as glycine and the metal ion, magnesium, are usually present in the solution to facilitate the reaction. Intravenous injection of these materials, obtained commercially from Sigma Chemical Company, into dogs has produced no deliterious side effects.

If the light-opacity of blood prevents a sufficient quantity of light, in the form of liquid light, to activate hematoporphyrin within an athermatous plaque, replacement of blood with a more translucent blood substitute may be performed. Examples would include normal saline, dextrose in water, and Krebs-Ringer's solution. For replacement of blood within the entire vascular tree or within blood vessels to vital organs, perfluorocarbon emulsion-containing blood substitutes, such as Fluosol-DA, may be used. Fluosol-DA carries oxygen in a manner similar to hemoglobin and has been approved by the FDA for use in clinical trials. For examples of the use of Fluosol-DA as a blood substitutes, see Engelman et al, *Ann Thorac Surg* 32: 528–535 (1981), Kanter et al, *Circulation* 64:75-83 (1981).

An advantage in the use of liquid light to activate hematophorphyrin within atheromatous plaques is that, once the liquid light has mixed in sufficient quantity with blood or a blood substitute throughout the vascular tree, it would be unnecessary to know the location of the plaques in order to lyse all plaques within the entire vascular tree. An other advantage is that a catheterization procedure would be unnecessary to deliver the light to a plaque in a vessel segment of interest.

The invention may be embodied in other specific forms without departing from the spirit or essential characteristics thereof. The present embodiments are therefore to be considered in all respects as illustrated and not restricted, the scope of the invention being indicated by the appended claims rather than by the foregoing description and all changes which come within the meaning and range of equivalency of the claims are therefore intended to be embraced therein.

I claim:

1. A method for the treatment of atherosclerosis in a mammal by destruction of atheromatous plaque in a diseased blood vessel, said process comprising:
    injecting a hematoporphyrin into the mammal to be treated for selective uptake into the atheromatous plaque;
    inserting a light-emitting catheter into the diseased vessel so that the light-emitting portion of the catheter is adjacent the atheromatous plaque to be lysed; and
    exposing the hematoporphyrin within said atheromatous plaque to light transmitted through the catheter for lysis of the plaque.

2. The method of claim 1 wherein the catheter is a balloon catheter and wherein said method further comprises illuminating the balloon and inflating the balloon to displace the blood between the illuminated balloon and the atheromatous plaque to be lysed.

3. The method of claim 1 wherein said injection is intravenous.

4. The method of claim 1 wherein said source of said illumination is a dye laser.

5. The method of claim 1 wherein said hematoporphyrin is an acetic acid-sulfuric acid derivative of hematoporphyrin.

6. The method of claim 2 wherein said balloon inflation is intermittent.

7. The method of claim 6 wherein the balloon is intermittently inflated responsive to ECG-gating so as to minimize interference with blood flow.

8. The method of claim 7 wherein the balloon is illuminated only when inflated.

* * * * *